United States Patent [19]

Podszun et al.

[11] 4,389,507

[45] Jun. 21, 1983

[54] FILLER-CONTAINING BEAD POLYMERS

[75] Inventors: Wolfgang Podszun, Cologne; Carlhans Süling, Odenthal; Michael Walkowiak, Leverkusen; Hans-Hermann Schulz, Leichlingen, all of Fed. Rep. of Germany

[73] Assignee: Bayer AG, Leverkusen, Fed. Rep. of Germany

[21] Appl. No.: 298,784

[22] Filed: Sep. 2, 1981

Related U.S. Application Data

[63] Continuation of Ser. No. 93,293, Nov. 13, 1979, abandoned.

[30] Foreign Application Priority Data

Nov. 14, 1978 [DE] Fed. Rep. of Germany ....... 2849279
Nov. 17, 1978 [DE] Fed. Rep. of Germany ....... 2849936

[51] Int. Cl.³ ............................................. C08L 31/00
[52] U.S. Cl. .................................... 524/460; 524/832
[58] Field of Search ........................ 524/832, 459, 460

[56] References Cited

U.S. PATENT DOCUMENTS

| 3,069,375 | 12/1962 | Bulitt, Jr. et al. | 525/510 |
| 3,716,505 | 2/1973 | Ohe et al. | 524/733 |
| 4,071,670 | 1/1978 | Vanzo et al. | 526/88 |
| 4,157,323 | 6/1979 | Yen et al. | 524/498 |

FOREIGN PATENT DOCUMENTS 1202046 8/1970 United Kingdom.

*Primary Examiner*—Lewis T. Jacobs
*Attorney, Agent, or Firm*—Connolly and Hutz

[57] ABSTRACT

Polymer beads having an average bead diameter of from 5 to 500 $\mu$, consisting of an inorganic fine-particled filler and polymerized (meth)acrylic acid esters, and a process for their production, wherein a mixture of monomer and, optionally, polymer which is soluble in the monomer, which has a viscosity of from 0.1 to 10 Pa.s, measured at the dispersion temperature, and filler is suspended in an aqueous medium in the presence of dispersants and is polymerized.

8 Claims, 2 Drawing Figures

FILLER-CONTAINING BEAD POLYMERS

This application is a continuation of application Ser. No. 093,293 filed Nov. 13, 1979, and now abandoned.

This invention relates to a process for the production of bead polymers based on (meth)acrylic acid esters which are filled with inorganic filler and are optionally crosslinked and have an average bead diameter ($d_{50}$) of from 5 to 500 μm.

The production of unfilled bead polymers by bead polymerisation is known, for example, from Houben-Weyl, Methoden der Organischen Chemie, Volume XIV/1. For this purpose, the monomer or monomers is or are suspended in water with stirring and the droplets formed are polymerised by means of a monomer-soluble initiator.

Dispersants are generally needed for bead polymerisation. They prevent the beads from sticking together during the reaction. They are generally water-soluble, high molecular weight organic compounds or finely divided, water-insoluble inorganic compounds. The latter are also known as Pickering dispersants. Many different substances are used as Pickering dispersants, for example the carbonates, phosphates, sulphates and silicates of the alkaline earth metals, aluminum oxide and the aluminum hydroxide, bentonite and talcum.

With these substances, the particles of the dispersant are not contained inside the beads but are virtually all located on the surface of the beads so that they can easily be removed during the working up process. Very pure bead polymers can be obtained in this way.

Attempts have already been made in some cases to polymerise dyes and pigments into bead polymers. Thus, it is known from U.S. Pat. No. 2,533,196 that pigmented polymer beads can be produced from dicarboxylic acid diallyl ester. When working in accordance with U.S. Pat. No. 2,533,196, polymerisation of the monomeric dicarboxylic acid diallyl ester is initiated and the substance is reacted with a pigment. The thickened pigmented composition is suspended in an aqueous sodium bisulphite or sodium nitrate solution and cured with stirring. In this process, the dispersant must be of the same thickness as the pigmented composition which has begun to polymerise.

Furthermore, a process for the production of polymerisation plastics materials containing luminous ink is described in German Pat. No. 829,221, in which process the suspension polymerisation is carried out in the presence of luminous paints and a thickener.

U.S. Pat. No. 2,533,196 and German Pat. No. 829,211 make use of the fact that highly viscous liquids retain solids which are worked into them more strongly than less viscous liquids.

The problems encountered in the bead polymerisation of highly viscous substances are known. The droplets of liquid formed increasingly tend to agglomerate and large beads, i.e. those which are from 1 to several millimeters large, are mainly formed (see also French Pat. No. 1,005,601). In the bead polymerisation of polymer/monomer mixtures filled with an inorganic filler, the increased tendency of the filled droplets of liquid to deposit sediment has an additional adverse effect on the formation of relatively small round polymer beads. It is not, therefore, possible to produce beads filled with inorganic filler and having an average bead diameter of less than 1 mm by working in accordance with U.S. Pat. No. 2,533,196 of German Pat. No. 829,221. Particles having diameters of several millimeters, whose shape differs greatly from the spherical shape are obtained in corresponding experiments.

The present invention therefore relates to the production of regular bead polymers based on methacrylic acid esters and/or acrylic acid esters, filled with inorganic filler and having an average diameter ($d_{50}$) of from 5 to 500 μ.

It has been found that bead polymers of this type are obtained if mixtures of monomer and, optionally polymer which is soluble in the monomer, which have a viscosity of from 0.1 to 10 Pa.s, measured at the dispersion temperature, and filler are suspended in an aqueous medium in the presence of a dispersant and are polymerised.

DESCRIPTION OF THE INVENTION

Figure 1:
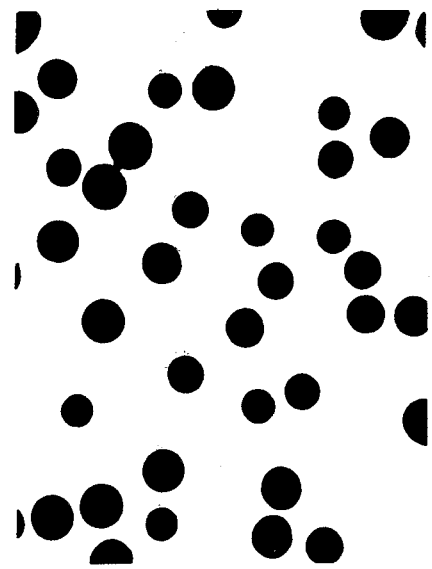
FIG. 1 is an illustration of a photomicrograph in bright field of filled particles of the 40–63μ fraction and FIG. 2 is an illustration of a photomicrograph of an unfilled bead polymer.

Filled heat polymers which are produced by the method according to the invention are suitable for use as a filler in paste-form dental compositions. They are readily wetted by the liquid paste component (monomer) and display good mechanical anchoring in the plastic matrix after the curing operation.

In the first operating step of the process according to the invention, the inorganic filler is worked into a viscous mixture of monomer liquid and polymer or into a viscous monomer liquid with vigorous stirring. The monomer phase should have a viscosity of from 0.1 to 10 Pa.s. The numerical data apply to the temperature at which the mass is dispersed. At visosities below 0.1 Pa.s, none of the inorganic particles or only a very small quantity of the inorganic particles are incorporated during the subsequent polymerisation process. At viscosities higher than 10 Pa.s small beads cannot be obtained, i.e. the monomer phase must have a defined viscosity for the technical effect.

Suitable monomers include the aliphatic esters of methacrylic acid and acrylic acid such as, for example, methyl(meth)acrylate, ethyl(meth)acrylate or cyclohexyl methacrylate, and suitable crosslinking agents include methacrylic acid esters of polyhydric alcohols such as ethylene glycol dimethacrylate, tetraethylene glycol dimethacrylate and trimethylol propane trimethacrylate. Up to 20% by weight of other monomers such as styrene, divinylbenzene or vinyl acetate can be used in addition to (meth) acrylates.

When these monomers are used, the viscosity generally has to be increased by partial polymerisation or by addition of some polymer which is soluble in the monomer and is produced separately.

Monomers having a sufficiently high viscosity can also be used. Examples of these include bis-GMA (reaction product of bisphenol A and glycidyl methacrylate) or urethane (meth)acrylates produced by addition of diisocyanates and hydroxyalkyl (meth)acrylates.

Finely divided inorganic substances which are insoluble in water are suitable as fillers, for example metal oxides, sulphates, silicates and phosphates as well as glasses and ceramic compositions and mixtures thereof. The particle diameter of the fillers is, generally, less than 5 μm, preferably less than 2 μm.

In the second operating step, the viscous mixture filled with inorganic filler is mixed with an initiator substance (for example benzoyl peroxide or cyclohexyl percarbonate) and suspended by high-speed stirring in an aqueous solution of, for example, a high molecular dispersant. The dispersant solution, generally, has a dispersant content of from 0.2 to 5% by weight. The suspension process generally takes place at room temperature (20° to 25° C.). The negative temperature coefficient of the viscosity can definitely be utilized in some cases in that mixtures whose viscosity is too high at room temperature (i.e. higher than 100 Pa.s) are suspended at elevated temperature.

Copolymers of vinyl alcohol/vinylacetate obtained by partial saponification or methacrylic acid/methacrylic acid methyl ester copolymers produced by copolymerisation are particularly suitable as dispersants.

In the third operating step, the suspension is polymerised with stirring by heating it to the decomposition temperature of the initiator substance. In this process, it is advantageous to heat the mixture under pressure in order to obtain particularly uniform beads.

The bead polymer can be obtained from the polymerised suspension in a conventional manner by filtration, washing and drying.

The viscosities indicated in the Examples have been determined at 25° C. using a falling-ball viscosimiter. The values each apply to the monomer phase in the absence of the inorganic filler.

EXAMPLE 1

Production of a bead polymer filled with magnesium hydroxide carbonate.

Reaction container

A 3-liter surface grinding beaker with a blade stirrer, reflux condenser, internal thermometer, gas inlet pipe and gas outlet pipe.

| Mixture 1: | Monomer phase | |
|---|---|---|
| | 220 g methyl methacrylate | Viscosity of the mixture: 0.6 Pa.s. |
| | 30 g ethylene glycol dimethacrylate | |
| | 50 g methyl methacrylate polymer ($[\eta]$ = 1.05 in chloroform) | |
| | 100 g magnesium hydroxide carbonate (4 MgCO$_2$.Mg(OH)$_2$.4 H$_2$O) (Manufacturer: Ridel de Haen AG) | |
| Mixture 2: | Aqueous phase | |
| | 15 g Moviol 70/88 (Farbwerke Hoechst) dissolved in 1000 ml distilled water. | |

The components of mixture 1 are introduced into the reaction container in the absence of atmospheric oxygen and stirred at 250 r.p.m. for 12 hours at room temperature, in which process the polymer is dissolved and a highly viscous composition is formed. This mixture is mixed with 2.2 g of cyclohexyl percarbonate and stirred for a further 30 minutes. The mixture 2 is then added all at once and the stirring speed is increased to 800 r.p.m. The suspension formed is heated to 70° C. and is cooled as the exothermic reaction is initiated to a sufficient extent for the temperature to be maintained below 85° C. Upon completion of the reaction, the mixture is kept at 85° C. for 2 hours with further stirring. The solid bead polymer is filtered off after cooling, washed several times with distilled water and dried at 50° C.

Yield: 328 g.
Average particle size: 160μ.

0.5 g of the bead polymer are treated with 20 ml of 1 N hydrochloric acid for 30 minutes at 70° C., then washed with distilled water and dried. Magnesium hydroxide carbonate which is not firmly incorporated in the beads is removed by this process. After the hydrochloric acid treatment, the magnesium hydroxide carbonate content of the beads is 14.1% by weight.

EXAMPLE 2

(Comparison Example)

Bead polymerisation without incorporation of magnesium hydroxide carbonate.

Reaction Container

As in Example 1.

| Mixture 1: | Monomer phase | |
|---|---|---|
| | 270 g methyl methacrylate | Viscosity of the mixture: 0.001 Pa.s |
| | 30 g ethylene glycol dimethacrylate | |
| | 100 g magnesium hydroxide carbonate (4 MgCO$_3$.Mg(OH)$_2$.4 H$_2$O) (Manufacturer: Riedel de Haen AG) | |
| Mixture 2: | Aqueous phase as in Example 1 | |

Mixture 1 is introduced into the reaction vessel in the absence of air and is mixed with 2.7 g of cyclohexyl percarbonate with slow stirring. Mixture 2 is then added all at once and the stirring speed is adjusted to 800 r.p.m. The rest of the process is carried out as in Example 1. 277 g of bead polymer having an average particle size of 42μ are obtained. After the hydrochloric acid treatment described in Example 1, the bead polymer contains no magnesium hydroxide carbonate. (The analytical error is smaller than 0.05%).

EXAMPLE 3

Production of a bead polymer filler with titanium dioxide.

Reaction container

As in Example 1.

| Mixture 1: | Monomer phase | |
|---|---|---|
| | 225 g methyl methacrylate | Viscosity of the mixture: 1.5 Pa.s. |
| | 15 g ethylene glycol dimethacrylate | |
| | 60 g methyl methacrylate polymer ($[\eta]$ = 1.05 in chloroform) | |
| | 150 g titanium dioxide (Bayer AG) | |
| Mixture 2: | Aqueous phase | |
| | 700 ml distilled water | |
| | 300 ml MMA-MAS dispersant solution [7.5% aqueous solution of a copolymer composed of equal parts by weight of methacrylic acid and methyl methacrylate with pH = 6 (adjusted using NaOH) and a viscosity of 3.6 Pa.s.] | |

The components of mixture 1 are introduced into the reaction container in the absence of atmospheric oxygen and stirred at 250 r.p.m. for 12 hours at room temperature, in which process the polymer is dissolved and a high-viscosity composition is formed. This mixture is wiped with 1.5 g of lauroyl peroxide and 1.5 g of benzoyl peroxide and stirred for a further 30 minutes. Mixture 2 is then added all at once and the stirring speed is increased to 800 r.p.m. The suspension formed is heated to 80° C. and is cooled as the exothermic reaction begins to a sufficient extent for the temperature to be maintained below 88° C. Upon completion of the reaction, the mixture is maintained at 85° C. for 2 hours with further stirring. After cooling, the solid bead polymer is freed from finely divided contents by decantation and is then filtered, washed several times with distilled water and dried at 50° C.

Yield: 407 g.
Combustion residue: 32.2%.
Screen analysis:
>200μ: 7.02%
100–200μ: 48.76%
63–100μ: 26.32%
40–63μ: 11.06%
0–40μ: 6.84%

FIG. 1 shows the 40 to 63μ fraction in a microscopic photograph in the bright field on a scale of 133:1. The beads appear dark owing to the strong light scattering of the $TiO_2$ particles. The filler is uniformly distributed.

Figure 2:
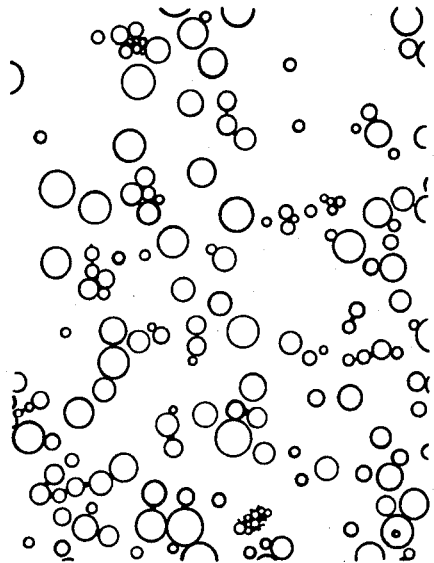

FIG. 2 shows a photograph of an unfilled bead polymer according to Example 2 by way of comparison, also as a bright fixed photograph on a scle of 133:1.

EXAMPLE 4

Production of a bead polymer filled with barium sulphate.
Reaction Vessel as in Example 1.

| Mixture 1: | Monomer phase | |
|---|---|---|
| | 220 g methyl methacrylate | Viscosity of the mixture: 0.6 Pa.s |
| | 30 g ethylene glycol dimethacrylate | |
| | 50 g methyl methacrylate polymer ([η] = 1.05 in chloroform) | |
| | 100 g barium sulphate (Riedel de Haen AG) | |
| Mixture 2: | Aqueous phase as in Example 3 | |

The components of mixture 1 are introduced into the reaction container in the absence of atmospheric oxygen and stirred at room temperature until the polymer has dissolved. The mixture obtained is mixed with 1.1 g of lauroyl peroxide and 1.1 g of benzoyl peroxide and, as described in Example 3, polymerised and worked up.

Yield: 375 g.
Combustion residue: 28.8%.
Screen analysis
>200μ:2.38%
100–200μ:2.44%
63–100μ:13.92%
40–63μ:38.06%
0–40μ:43.20%

EXAMPLE 5

Production of a bead polymer filled with zirconium dioxide.
Reaction container: A 6-liter autoclave with double anchor stirrer

| Mixture 1: | Monomer phase | |
|---|---|---|
| | 580 g methyl methacrylate | Viscosity of the mixture: |
| | 30 g ethylene glycol dimethacrylate | |

| | | |
|---|---|---|
| | 110 g methyl methacrylate polymer ([η] in chloroform = 2.0) | 6 Pa.s. |
| | 100 g zirconium dioxide (E. Merck, Darmstadt) | |
| Mixture 2: | Aqueous phase | |
| | 2100 ml distilled water | |
| | 900 ml MMA-MAS-dispersant solution, as described in Example 3. | |

The components of mixture 1 are introduced into the autoclave in the absence of air and stirred at 100 r.p.m. for 12 hours at room temperature. This mixture is mixed with 3 g of lauroyl peroxide and 3 g of benzoyl peroxide and stirred for a further 30 minutes. After the addition of mixture 2, 15 bar of nitrogen is applied, the stirring speed is adjusted to 450 r.p.m. and the mixture is heated to 80° C. As the reaction begins, the mixture is cooled sufficiently for the temperature to remain below 90° C. The mixture is then stirred for a further 2 hours at 80° C. The bead polymer is filtered after cooling, washed several times with distilled water and dried at 50° C.

Yield: 802 g.
Combustion residue: 12.5%.
Screen analysis:
>200μ:26.00%
100–200μ:30.24%
63–100μ:21.20%
40–63μ:13.22%
0–40μ:9.34%

EXAMPLE 6

Production of a bead polymer filled with silica. Reaction container: as in Example 1

| Mixture 1: | Monomer phase | |
|---|---|---|
| | 188 g bisphenol-A-bis-(3-methacrylato-2-hydroxypropyl)ether | Viscosity of the mixture: about 1 Pa.s |
| | 112 g triethylene glycol dimethacrylate | |
| | 33 g highly dispersed silica (BET specific surface area 170 m$^2$/g) | |
| Mixture 2: | Aqueous phase | |
| | 700 ml distilled water | |
| | 300 ml MMA-MAS dispersant solution as described in Example 3. | |

Mixture 1 is mixed with 3.0 g of benzoyl peroxide and polymerised in the manner described in Example 3.
Yield: 305 g.
Combustion residue: 9.5%.
Screen analysis:
>100μ:0.68%
63–100μ:7.56%
40–63μ:34.16%
0–40μ:57.60%

EXAMPLE 7

Production of a bead polymer filled with silica and barium sulphate.
Reaction container: as in Example 1.

Mixture 1

300 g Plex 6661 manufactured by Messrs. Rohm, Darmstadt (Reaction product of trimethyl hexamethylene diisocyanate and 2-hydroxyethyl methacrylate), viscosity 7.5 Pa.s.

30 g highly dispersed silica (BET specific surface area 170 m²/g).

100 g barium sulphate (Riedel de Haen).

Mixture 2

700 ml distilled water.

300 ml MMA-MAS dispersant solution, as described in Example 3.

Mixture 1 is mixed with 5 g of cyclohexyl percarbonate and polymerised, as described in Example 3.

Yield: 385 g.

Combustion residue: 25.5%.

Screen analysis:

>200μ:28.46%
100–200μ:46.82%
63–100μ:16.32%
40–63μ:5.52%
0–40μ:2.88%

We claim:

1. A process for the production of cross-linked bead polymers of (meth)acrylic acid esters and up to 20% by weight of other monomers, filled with a uniformly distributed inorganic filler and having an average diameter of from 5 to 500μ comprising
   (i) working inorganic filler into a monomer liquid or a mixture, of monomer liquid and polymer, said monomer or said mixture, respectively, having a viscosity of from 0.1 to 10 Pa.s at the dispersion temperature,
   (ii) adding a polymerization ititiator to the mixture of filler, monomer liquid and, optionally, polymer and suspending the mixture in an aqueous medium in the presence of a dispersant and
   (iii) polymerizing the suspension by heating it to the decomposition temperature of said initiator, said monomer liquid containing a cross-linking agent.

2. The process according to claim 1 wherein the monomer liquid consists of monomers having a viscosity of from 0.1 to 10 Pa.s.

3. The process according to claim 1 wherein the monomer liquid comprises a solution of polymer in monomer.

4. The process according to claim 3 wherein the solution has been prepared by partially polymerizing the monomer.

5. The process according to claim 1 wherein the cross-linking agent is selected from methacrylic acid esters of polyhydric alcohols.

6. The process according to claim 1 wherein the cross-linking agent is selected from the group of bis-GMA and urethane (meth)acrylates produced by addition of diisocyanates and hydroxyalkyl(meth)acrylates.

7. The process according to claim 1 wherein the monomer liquid contains between 4% and 100% by weight, of crosslinking agent.

8. Polymer beads having an average bead diameter of from 5 to 500μ and comprising 5 to 50 parts by weight of an inorganic, fine-particled filler and 95 to 50 parts by weight of polymerized (meth)acrylic acid esters produced by the process according to claim 1.

* * * * *